United States Patent [19]

Ludwig et al.

[11] Patent Number: 5,200,421

[45] Date of Patent: Apr. 6, 1993

[54] MICROBICIDAL ACTIVE COMPOUND COMBINATIONS

[75] Inventors: Georg-Wilhelm Ludwig, Krefeld; Otto Exner, Ratingen; Wilfried Paulus, Krefeld; Karl-Heinz Büchel, Burscheid; Graham Holmwood, Wuppertal, all of Fed. Rep. of Germany

[73] Assignee: Bayer Aktiengesellschaft, Leverkusen, Fed. Rep. of Germany

[21] Appl. No.: 867,955

[22] Filed: Apr. 13, 1992

[30] Foreign Application Priority Data

Apr. 23, 1991 [DE] Fed. Rep. of Germany ....... 4113158

[51] Int. Cl.$^5$ ...................... A01N 43/64; A01N 47/10
[52] U.S. Cl. .................... 514/383; 514/478; 514/479
[58] Field of Search ........... 514/383, 478, 479

[56] References Cited

U.S. PATENT DOCUMENTS 4,977,186 12/1990 Gruening ............................. 514/479

FOREIGN PATENT DOCUMENTS 0393746 10/1990 European Pat. Off. .

OTHER PUBLICATIONS

Patent Abstracts of Japan, vol. 13 No. 134, Apr. 4, 1989 p. 50 C 581.
Patent Abstract of Japan, vol. 12 No. 110, Apr. 8, 1988 p. 146 C 486.
Patent Abstracts of Japan, vol. 16 No. 40, Jan. 31, 1992 p. 15 C 906.

Primary Examiner—Allen J. Robinson
Attorney, Agent, or Firm—Sprung Horn Kramer & Woods

[57] ABSTRACT

New synergistic microbicidal active compound combinations, and the use thereof, comprising an azole fungicide, such as tebuconazole, and an iodopropargyl derivative, such as IPBC, if appropriate with the addition of other active compounds.

7 Claims, No Drawings

MICROBICIDAL ACTIVE COMPOUND COMBINATIONS

The present invention relates to new microbicidal synergistic active compound combinations of known azole fungicides and known iodopropargyl derivatives.

It is known that imidazole fungicides or triazole fungicides, such as, for example, α-[2-(4-chlorophenyl)-ethyl]-α-(1,1-dimethylethyl)-1-H-1,2,4-triazole-1-ethanol (tebuconazole) and 1-[[2-(2,4-dichlorophenyl)-4-n-propyl-1,3-dioxolan-2-yl]-methyl]-1-H-1,2,4-triazole (propiconazole), can be used as such or in the form of their salts for protecting plants and seeds (compare, for example, EP-A-0 040 345 and EP-A-0 052 424). It is furthermore known that these compounds are also suitable for use in wood preservation for combating wood-destroying or wood-discolouring microbes (compare, for example, DE-OS (German published specification) 3,621,494 and U.S. Pat. No. 4,079,062). The azole fungicides, such as the tebuconazole mentioned, has its action potencies against Basidiomycetes (wood-destroying organisms), but weaknesses against Ascomycetes (wood-discolouring organisms, blueing fungi.)

It is furthermore known that iodopropargyl derivatives, such as, for example, 3-iodo-2-propinyl n-butylcarbamate (IPBC)., are suitable for use in wood preservation (compare DE-OS (German published specification) 2,433,410). These compounds are very active against blueing fungi. However, they are unsatisfactory in their individual use against microorganisms, since their action spectrum has gaps.

It is furthermore known that mixtures of IPBC and didecyldimethylammonium chloride can be used for protection against wood-destroying fungi, in particular brown rot and white rot fungi, and wood-discolouring fungi and against termites (compare AU 8656-411). Moulds and mildew can also be combated with these.

It is moreover known that IPBC in combination with an azole derivative, such as, for example, 1-[2-(2,4-dichlorophenyl) -1,3-dioxolan-2-yl-methyl]-1H-1,2,4-triazole [azaconazole] can be incorporated as a fungicidal active compound into wood-preserving paints (compare DE-OS (German published specification) 3,414,244).

The known azole fungicides and the known mixtures have gaps in their action. They are therefore unsuitable for protecting industrial materials from attack by microorganisms, since industrial materials are always exposed to attack by a large number of different microorganisms, so that reliable protection can be achieved only by using microbicides having a broad action spectrum or with microbicide combinations which have a composition such that a broad action spectrum results.

It has now been found that new active compound combinations of at least one azole fungicide, such as, for example, 1-(4-chlorophenoxy)-3,3-dimethyl-1-(1H-1,2,4-triazo-1-yl)-2-butanones (triadimefone)

β-(4-chlorophenoxy)-α-(1,1 dimethyl-ethyl)-1H-1,2,4-triazoles-1-ethanol (triadimenol)

±α-[2-(4-chlorophenyl)-ethyl]-α-(1,1 dimethylethyl)-1H-1,2,4-triazole-1-ethanol (tebuconazole)

(RS)-2-(2,4-dichlorophenyl)-1-(1H-1,2,4-triazol-2-yl)-hexan-2-ol (hexaconazole)

1-(N-propyl-N-(2-(2,4,6-(trichlorophenoxy)-ethyl)-carbamoyl)-imidazole (prochloraz), metal salts or acid addition compounds thereof and, in the cases where the compound has an asymmetric carbon atom, also the isomers and isomer mixtures of the most diverse compositions, especially preferably ±α-[2-(4-chlorophenyl)-ethyl]-α-(1,1-dimethylethyl)-1H-1,2,4-triazole-1-ethanol (tebuconazole) and at least one iodopropargyl derivative of the formula (I)

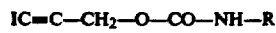

IC≡C—CH₂—O—CO—NH—R  (I)

in which

R represents straight-chain or branched alkyl having 1 to 6 carbon atoms, or represents cycloalkyl having 3 to 6 carbon atoms or represents aryl, preferably phenyl, have a particularly high microbicidal activity. Examples which may be mentioned are, for example: 3-iodo-2-propinyl n-butylcarbamate (IPBC) 3-iodo-2-propinyl n-hexylcarbamate 3-iodo-2-propinyl cyclohexylcarbamate and 3-iodo-2-propinyl phenylcarbamate, 3-iodo-2-propinyl n-butylcarbamate (IPBC) being especially preferred.

Surprisingly, the microbicidal activity, and in particular the fungicidal activity, of the active compound combinations according to the invention is considerably higher than the sum of the actions of the individual active compounds. A true synergistic effect thus exists. The active compound combinations represent a valuable enrichment of the art.

The combination of tebuconazole and IPBC is to be singled out in particular.

The azole fungicides can be present not only in the form of free bases but—as already mentioned—in the form of their metal salt complexes or as acid addition salts.

Preferred possible metal salts are salts of metals of main groups II to IV and sub-groups I and II and IV to VII of the periodic system, examples which may be mentioned being copper, zinc, manganese, magnesium, tin, iron, calcium, aluminium, lead, chromium, cobalt and nickel.

Possible anions of the salts are those which are preferably derived from the following acids: hydrohalic acids, such as, for example, hydrochloric acid and hydrobromic acid, and furthermore phosphoric acid, nitric acid and sulphuric acid.

The metal salt complexes of the azole fungicides can be obtained in a simple manner by customary processes, thus, for example, by dissolving the metal salt in alcohol, for example ethanol, and adding the solution to the azole fungicide. The metal salt complexes can be isolated in a known manner, for example by filtration, and if appropriate purified by recrystallisation.

The following acids are preferably suitable for the preparation of acid addition salts of the azole fungicides: the hydrohalic acids, such as, for example, hydrochloric acid and hydrobromic acid, in particular hydrochloric acid, and furthermore phosphoric acid, nitric acid, sulphuric acid, mono- and bifunctional carboxylic acids and hydroxycarboxylic acids, such as, for example, acetic acid, propionic acid, butyric acid, mandelic acid, oxalic acid, succinic acid, 2-hydroxyethane-dicarboxylic acid, maleic acid, fumaric acid, tartaric acid, citric acid, salicylic acid, sorbic acid and lactic acid, as well as sulphonic acids, such as, for example, p-toluenesulphonic acid, 1,5-naphthalenedisulphonic acid and alkanesulphonic acids, and optionally substituted benzoic acids.

The acid addition salts of the compounds can be obtained in a simple manner by customary salt formation methods, for example by dissolving a compound in a suitable inert solvent and adding the acid, for example hydrochloric acid, and can be isolated in a known manner, for example by filtration, and if appropriate purified by washing with an inert organic solvent.

It is also possible for mixtures of different azole derivatives to be employed. These compounds and their preparation are known, and 1-hyroxyethyl-azole derivatives can thus be obtained, for example, from a suitable oxirane and a suitable azole, such as, for example, 1,2,4-triazole or imidazole (compare EP-A-0 40 345, EP-A-0 052 424 and DE-OS (German published specification) 2,551,560).

It is also possible to employ iodopropargyl derivative mixtures, and the active compounds of the formula (I) are also known and can be prepared by known processes, thus, for example, by iodinating suitable acetylenic alcohols and then preparing the corresponding carbamate by reaction of the reaction product with a suitable isocyanate (compare DE-OS (German published specification) 2,433,410).

The weight ratios of the active compounds in the active compound combinations can vary within relatively wide ranges.

The mixtures contain the azole components in amounts of from 0.1 to 99.9%, the remainder to make up 100% being the iodopropargyl compound.

The mixing ratio of azole component to iodopropargyl compound is preferably 1:9 to 9:1, particularly preferably 2.5:7.5 to 7.5:2.5.

The active compound combinations according to the invention have a potent action on microorganisms; they are active above all against moulds and wood-discolouring and wood-destroying fungi. The following groups of microorganisms may be mentioned as examples — but without specifying a limitation:

A: Wood-discolouring fungi:
 A1: Ascomycetes:
  Ceratocystis, such as *Ceratocystis minor*
 A2: Deuteromycetes:
  Aspergillus, such as *Aspergillus niger*
  Aureobasidium such as *Aureobasidium pullulans*
  Dactyleum such as *Dactyleum fusarioides*
  Penicillium such as *Penicillium brevicaule* or *Penicillium variabile*
  Sclerophoma such as *Sclerophoma pithyophila*
  Scopularia such as *Scopularia phycomyces*
  Trichoderma such as *Trichoderma viride* or *Trichoderma lignorum*
 A3: Zygomycetes:
  Mucor such as *Mucor spinorus*
B: Wood-destroying fungi:
 B1: Ascomycetes:
  Chaetomium such as *Chaetomium globosum* or *Chaetomium alba-arenulum*
  Humicola such as *Humicola grisea*
  Petriella such as *Petriella setifera*
  Trichurus such as *Trichurus spiralis*
 B2: Basidiomycetes
  Coniophora such as *Coniophora puteana*
  Coriolus such as *Coriolus versicolor*
  Donkioporia such as *Donkioporia expansa*
  Glenospora such as *Glenospora graphii*
  Gloeophyllum such as *Gloeophyllum abietinum* or *Goeophyllum adoratum* or *Gl. protactum* or *Gloeophyllum sepiarium* or *Gl. trabeum*
  Lentinus such as *Lentinus cyathiformes* or *Lentinus edodes* or *Lentinus lepideus* or *Lentinus grinus* or *L. squarrolosus*
  Paxillus such as *Paxillus panuoides*
  Pleurotus such as *Pleurotis ostreatus*
  Poria such as *Poria monticola* or *Poria placenta* or *Poria vaillantii* or *Poria vaporaria*
  Serpula such as *Serpula himantoides* or *Serpula lacrymans*
  Stereum such as *Stereum hirsutum*
  Tyromyces such as *Tyromyces palustris*
 B3: Deuteromycetes
  Alternaria such as *Alternaria tenius*
  Cladosporium such as *Cladosporium herbarum*

The active compound combinations, agents, concentrates or generally formulations according to the invention and corresponding use forms have potent microbicidal actions. They can therefore be used for preserving wood and timber products against microorganisms, for example against wood-destroying or wood-discolouring fungi.

By wood which can be preserved by the mixtures according to the invention there is to be understood, for example: structural timber, wooden beams, railway sleepers, telegraph poles, wooden fences, wood panelling, wooden windows and doors, plywood, chipboard, joinery work or wood products used quite generally in house construction or building joinery.

The new active compound combinations can be used as such in the form of concentrates or generally customary formulations and the use forms prepared therefrom, such as solutions, suspensions, emulsions or pastes.

Particularly effective preservation of wood is achieved by large-scale industrial impregnation processes, for example vacuum, double vacuum - or pressure processes.

The amount of active compound combinations employed depends on the nature and occurrence of the microorganisms, the germ count and the medium. The optimum amount employed can in each case be determined for the use by test series. In general, however, it is sufficient to employ 0.001 to 5% by weight, preferably 0.05 to 1% of the active compound mixtures, based on the material to be protected. The formulations mentioned can be prepared in a manner which is known per se, for example by mixing the active compounds with a solvent or diluent and/or binder or fixing agent, if appropriate siccatives and UV stabilisers and if appropriate dyestuffs and pigments, as well as other processing auxiliaries.

Possible solvents or diluents are organochemical solvents or solvent mixtures and/or a polar organic solvent or solvent mixtures and/or an oily or oil-like organochemical solvent or solvent mixture and/or water with at least one emulsifier and/or wetting agent. The particular mineral oils/mineral oil-containing solvent mixtures or aromatic fractions thereof are preferably used as the customary low-volatility, water-insoluble oily or oil-like solvents. Examples which may be mentioned are test benzine, petroleum or alkylbenzenes, and in addition spindle oil and monochloronaphthalene. The boiling ranges of these low-volatility solvent (mixtures) cover the range from about 170° C. to not more than 350° C.

The low-volatility oily or oil-like solvents described above can be replaced in part by more highly volatile organochemical solvents.

Some of the solvent or solvent mixture described above is preferably replaced by a polar organochemical solvent or solvent mixture for the preparation of a wood preservative according to the invention. Solvents which contain hydroxyl groups, ester groups, ether groups or mixtures of this functionality are preferably employed here. Examples which may be mentioned are esters or glycol ethers. As binders according to the invention there are to be understood synthetic resins or binding drying oils which are water-dilutable or soluble, dispersible or emulsifiable in organochemical solvents, for example products based on acrylic resins, vinyl resins, polyester resins, polyurethane resins, alkyd resins, phenolic resins, hydrocarbon resins or silicone resins. The binder used can be employed as a solution, emulsion or dispersion. Mixtures of alkyd resins and drying vegetable oil are preferably used. Alkyd resins with an oil content of between 45 and 70% are particularly preferred.

All or some of the binder mentioned can be replaced by a fixing agent (mixture) or a plasticiser (mixture). These additives are intended to prevent evaporation of the active compounds and crystallization or precipitation. They preferably replace 0.01 to 30% of the binder (based on 100% of the binder employed).

The plasticizers originate from the chemical classes or phthalic acid esters, such as dibutyl, dioctyl or benzylbutyl phthalate, phosphoric acid esters, such as tributyl phosphate, adipic acid esters, such as di-(2-ethylhexyl) adipate, stearates, such as butyl stearate and amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether, or ketones, such as benzophenone or ethylbenzophenone.

To the active compound combinations according to the invention or the agents, concentrates or quite generally formulations which can be prepared therefrom, can be mixed also with further microbicides, fungicides, insecticides or other active compounds in order to increase the active compound spectrum or to achieve particular effects. Those mixtures can have a still broader spectrum of activity than the invention combinations. In many cases synergistic effects are achieved, this means, the activity of the mixture is greater than the activity of the individual compounds. Particularly favourable mixing partners are, for example, the following compounds:

Sulphenamides, such as Dichlofluanid (Euparen), Tolylfluanid (Methyleuparen), Folpet, Fluorfolpet;

Benzimidazoles, such as Carbendazim (MBC), Benomyl, Fuberidazole, Thiabendazole or their salts;

Thiocyanates, such as Thiocyanatomethylthiobenzothiazole (TCMTB), Methylenbisthiocyanate (MBT);

Quaternary ammonium compounds, such as benzyldimethyl-tetradecylammoniumchloride, Benzyldimethyl-dodecyl-ammoniumchloride, Didecyldimethyl-ammoniumchloride;

Morpholinderivatives, such as $C_{11}-C_{14}$-4-alkyl-2,6-dimethylmorpholine-homologues (Tridemorph), ($\pm$)-cis-4-[3-tert-butylphenyl) -2-methylpropyl]-2,6-dimethyl-morpholine (Fenpropimorph), Falimorph);

Phenols, such as o-phenylphenol, tribromphenol, tetrachlorphenol, pentachlorphenol, 3-methyl-4-chlorphenol, dichlorophen, Chlorophen or their salts;

Iododerivatives such as diiodmethyl-p-arylsulfone for example diiodmethyl-p-tolylsulfone;

Bromoderivative such as Bronopol;

Isothiazolinones, such as N-methylisothiazolin-3-on, 5-chloro-N-methylisothiazolin-3-on, 4,5-dichloro-N-octylisothiazolin-3-on, N-octylisothiazolin-3-on (octhilinone);

Benzisothiazolinones, cyclopentenisothiazolinones;

Pyridines, such as 1-hydroxy-2-pyridinthion (or their Na-, Fe-, Ma, Zn-salts), tetrachlor-4-methylsulphonyl-pyridin;

Metallic soaps, such as tin-, copper-, zinc-naphthenate, -octoate, -2-ethylhexanoat, -oleate, -phosphate, -benzoate, oxides, such as TBTO, $Cu_2O$, CuO, ZnO;

Organic tin-derivatives, such as tributyltin naphthenate or tributyl tinoxide;

Dialkyldithiocarbamates such as Na- and Zn-sals of dialkyldithiocarbamates, tetramethyldiuramdisulfides (TMTD);

Nitriles, such as 2,4,5,6-tetrachlorisophthalonitrile (Chlorthanlonil); microbicides with active halogen groups, such as Cl-Ac, MCA, Tectamer, Bronopol, Bromidox;

Benzthiazoles, such as 2-Mercaptobenzothiazoles; Dazomet; chinolines such as 8-hydroxyquinoline;

Compounds which cleave of formaldehyde, such as benzylalcoholmono(poly)hemiformal, oxazolidine, hexahydro-s-triazine, N-methylolchloracetamid;

Tris-N-(cyclohexyldiazeniumdioxy)-aluminum N-(cyclohexyldiazeniumdioxy)-tributyl tin or K-salts; Bis-(N-cyclohexyl)diazinium (-dioxy- copper or aluminum);

As insecticides are preferred:

Phosphorous acid esters, such as zinphos-ethyl, azinphos-methyl, 1-(4-chlorphenyl)-4-(O-ethyl, S-propyl) phosphoryloxypyrazol (TIA-230); Chlorpyrifos, Coumaphos, Demeton-S-methyl, Diazinon, Dichlorvos, Dimethoate, Ethoprophos, Eltrimfos, Feniltrothion, Fenthion, Heptenophos, Parathion, Parathion-methyl, Phosalone, Phoxim, Pirimphos-ethyl, Pirimiphosmethyl, Profenofos, Prothiofos, Sulfprofos, Triazophoas and Trichlorphon;

Carbamates, such as Aldicarb, Beniocarb, BPMC (2-(1-methylpropyl) phenylmethylcarbamate), Butocarboxim, Butoxicarboxim, Carbaryl, Carbofuran, Carbosulfan, Cloethocarb, Isoprocarb, Methomyl, Oxamyl, Pirimicarb, Promecarb, Propoxur and Thidicarb;

Pyrethroids such as Allethrin, Alphamethrin, Bioresmethrin, Byfenthrin (FMC 54 800), Cycloprothrin, Cyfluthrin, Decamthrin, Cyhalothrin, Cypermethrin, Deltamethrin, AlPha-cyano-3-phenyl-2-methylbenzyl-2,2-dimethyl-3-(2-chlor-2-trifluormethylvinyl)cyclopropanpropancarboxylat, Fenpropathrin, Fenfluthrin, Fenvalerate, Flucythrinate, Flumthrin, Fluvalinate, Permethrin and Resmethrin;

Nitroimino and Nitromethylenes, such as 1-[6-chloro-3-pyridinyl)-methyl]-4,5-dihydro-N-nitro-1H-imidazol-2-amin (Imidacloprid)

Further active compounds are also algicides, molluscicides and compounds against "sea animals", which grow for example on ship coatings.

New agents or concentrates contain the active compound mixtures according to the invention in a concentration of 0.01 to 30% by weight, and in addition if appropriate 0.001 to 10% by weight of another suitable fungicide, insecticide or another active compound as mentioned above, as well as more than 30% by weight of a mixture of solvent/diluent and/or binders or fixing agents, if appropriate siccatives and UV stabilisers and if appropriate dyestuffs and pigments, as well as other processing auxiliaries.

The agents, concentrates and formulations according to the invention which are prepared in this manner and are intended for preserving wood and timber products display an activity not only against the abovementioned fungi but also against wood-destroying insects if an insecticide is present. Examples which may be mentioned of wood-destroying insects—without specifying a limitation—are:

A: Woodwasps:
*Sirex juvencus*
*Urocerus augur*
*Urocerus gigas*
*Urocerus gigas taignus*

B: Beetles:
*Anobium punctatum*
*Apate monachus*
*Bostrychus capucinus*
*Chlorophores pilosus*
*Dendrobium pertinex*
*Dinoderus minutus*
*Ernobius mollis*
*Heterobostrychus brunneus*
*Hylotrupes bajulus*
*Lyctus africanus*
*Lyctus brunneus*
*Lyctus linearis*
*Lyctus planicollis*
*Lyctus pubescens*
*Minthea rugicollis*
*Priobium carpini*
*Ptilinus pecticornis*
*Sinoxylon spec.*
*Trogoxylon aequale*
*Trypto dendron spec.*
*Xestobium rufovillosum*
*Xyleborus spec.*

C: Termites:
*Coptotermes formosanus*
*Cryptotermes brevis*
*Heterotermes indicola*
*Kalotermes flavicollis*
*Mastotermes darwiniensis*
*Recitulitermes flavipes*
*Reticulitermes lucifugus*
*Reticulitermes santonensis*
*Zootermopsis nevadensis*

The active compound combinations according to the invention allow, in an advantageous manner, the mircobicidal agents previously available to be replaced by more effective agents. They exhibit a good stability and have advantageous manner a broad action spectrum.

EXAMPLE

1. Synergistic fungicide mixture of tebuconazole (A) and IPBC (B)

30 parts by weight of tebuconazole and 70 parts by weight of IPBC are intimately mixed or ground together in a suitable mill as solids. The synergistic fungicide mixture results as a white powder.

Mixtures of the other mixing ratios of the components can be prepared analogously.

2. Synergistic activity of the active compounds according to the invention against wood fungi.

The synergistic activity of the active compound mixtures according to the invention can be carried out by comparing the MIC (minimum inhibitory concentration) values of the pure active compounds with those of the mixtures.

Determination of the MIC values:

To demonstrate the activity against fungi, the minimum inhibitory concentrations (MIC) of mixtures according to the invention were determined:

Active compounds according to the invention are added in concentrations of 0.1 mg/l to 5,000 ml/l to an agar prepared from beer wort and peptone. After the agar has solidified, it is contaminated with pure cultures of the test organisms listed in the table. After storage at 28° C. and 60 to 70% relative atmospheric humidity for 2 weeks, the MIC is determined. The MIC is the lowest concentration of active compound at which no growth at all of the species of microbe used takes place; it is stated in the following Table 1.

The synergism is then determined by the method described by Kull et al (F. C. Kull, P. C. Eismann, H. D. Sylvestrowicz, R. L. Mayer, Applied Microbiol. 9, 538 to 541, 1961). The following designations apply here:

$$\frac{Q_A}{Q_a} + \frac{Q_B}{Q_b} = X$$

$X = 1$ denotes additive characteristics
$X > 1$ denotes antagonism
$X < 1$ denotes synergism
$Q_a$ = concentration of substance A which represents the MIC
$Q_b$ = concentration of substance B which represents the MIC
$Q_A$ = amount of substance A in the concentration of A/B which suppresses growth of the microbe
$Q_B$ = amount of substance B in the concentration of A/B which suppresses growth of the microbe.

The result is recorded in the following Table 2.

TABLE 1

| Active compound | MIC values | | | |
| --- | --- | --- | --- | --- |
| | *Sclerophoma pityophila* | *Aureobasidium pullulans* | *Alternaria tenius* | *Cladosporium herbarum* |
| Tebuconazole | 1.5 | 35 | 200 | 50 |
| Tebu/IPBC = 9:1 | 1 | 35 | 50 | 50 |
| Tebu/IPBC = 8:2 | 1.5 | 20 | 20 | 20 |
| Tebu/IPBC = 7:3 | 1 | 7.5 | 15 | 12.5 |
| Tebu/IPBC = 6:4 | 1 | 5 | 10 | 10 |
| Tebu/IPBC = 5:5 | 0.75 | 5 | 7.5 | 10 |
| Tebu/IPBC = 4:6 | 0.75 | 7.5 | 12.5 | 5 |
| Tebu/IPBC = 3:7 | 0.5 | 2 | 3.5 | 2 |
| Tebu/IPBC = 2:8 | 0.75 | 7.5 | 5 | 5 |
| Tebu/IPBC = 1:9 | 0.75 | 7.5 | 7.5 | 5 |
| IPBC | 1 | 7.5 | 5 | 5 |

TABLE 2

| Tebuconazole/IPBC | Sclerophoma pityophila | Aureob. pull. | Altern. tenius | Clad. herbarum |
|---|---|---|---|---|
| 9:1 | 0.70 | >1 | >1 | >1 |
| 8:2 | 1.1 | 1 | 0.88 | ≥1 |
| 7:3 | 0.77 | 0.12 | 0.93 | 0.95 |
| 6:4 | 0.80 | 0.36 | 0.83 | 0.92 |
| 5:5 | 0.63 | 0.40 | 0.77 | 1.1 |
| 4:6 | 0.65 | 0.69 | >1 | 0.64 |
| 3:7 | 0.45 | 0.72 | 0.49 | 0.29 |
| 2:8 | 0.70 | 0.84 | 0.80 | 1 |
| 1:9 | 0.73 | 0.92 | >1 | ~1 |

We claim:

1. A fungicidally microbicidally active composition comprising a synergistic mixture of tebuconazole or a salt thereof and 3-iodo-2-propargyl n-butylcarbamate wherein the synergistic weight ratio of tebuconazole to 3-iodo-2-propargyl n-butycarbamate is from 1:9 to 9:1.

2. A composition according to claim 1, wherein said composition further comprises a solvent.

3. A composition according to claim 2, wherein said composition further comprises a binder.

4. A composition according to claim 3, wherein said composition further comprises a plasticizer.

5. A composition according to claim 1, further comprising at least one member selected from the group consisting of microbicides other than tebuconazole and 3-iodo-2-propargyl n-butylcarbamate has effective amount of a fungicide and an insecticide.

6. A method of combatting fungus microbes, comprising applying to such microbes or to a microbe habitat a fungicidally effective amount of the composition according to claim 1.

7. A method of preserving wood and timber products against fungus microorganisms, comprising applying to said wood and timber products a fungicidally effective amount of the composition according to claim 1.

* * * * *

UNITED STATES PATENT AND TRADEMARK OFFICE
CERTIFICATE OF CORRECTION

PATENT NO. : 5,200,421

DATED : April 6, 1993

INVENTOR(S) : Ludwig et al.

It is certified that error appears in the above-identified patent and that said Letters Patent is hereby corrected as shown below:

Col. 9, last line    Delete " butycarbamate " and substitute -- butylcarbamate --

Col. 10, line 10    Delete " has " and substitute -- an --

Signed and Sealed this

Thirteenth Day of September, 1994

*Attest:*

BRUCE LEHMAN

*Attesting Officer*    *Commissioner of Patents and Trademarks*